(12) United States Patent
Drew

(10) Patent No.: US 10,980,871 B2
(45) Date of Patent: Apr. 20, 2021

(54) VACCINE COMPOSITIONS

(71) Applicant: iosBio Ltd, West Sussex (GB)

(72) Inventor: Jeffrey Drew, West Sussex (GB)

(73) Assignee: iosBio Ltd, West Sussex (GB)

( * ) Notice: Subject to any disclaimer, the term of this patent is extended or adjusted under 35 U.S.C. 154(b) by 0 days.

(21) Appl. No.: 16/611,256

(22) PCT Filed: May 8, 2018

(86) PCT No.: PCT/GB2018/051226
§ 371 (c)(1),
(2) Date: Nov. 6, 2019

(87) PCT Pub. No.: WO2018/206930
PCT Pub. Date: Nov. 15, 2018

(65) Prior Publication Data
US 2020/0155665 A1  May 21, 2020

(30) Foreign Application Priority Data
May 8, 2017 (GB) .................................. 1707367

(51) Int. Cl.
| | | |
|---|---|---|
| A61K 39/00 | (2006.01) | |
| A61K 39/145 | (2006.01) | |
| A61K 39/39 | (2006.01) | |
| A61K 39/12 | (2006.01) | |
| C12N 7/00 | (2006.01) | |
| A61P 31/16 | (2006.01) | |
| A61K 9/19 | (2006.01) | |
| A61K 31/198 | (2006.01) | |

(52) U.S. Cl.
CPC .............. *A61K 39/145* (2013.01); *A61K 9/19* (2013.01); *A61K 31/198* (2013.01); *A61P 31/16* (2018.01); *C12N 7/00* (2013.01); *A61K 2039/55505* (2013.01); *A61K 2039/70* (2013.01); *C12N 2760/16134* (2013.01); *C12N 2760/16151* (2013.01); *C12N 2760/16234* (2013.01); *C12N 2760/16251* (2013.01)

(58) Field of Classification Search
CPC ....... A61P 31/16; A61K 39/145; A61K 39/39; A61K 39/12; A61K 2039/55566
See application file for complete search history.

(56) References Cited

U.S. PATENT DOCUMENTS

| | | |
|---|---|---|
| 3,927,208 A | 12/1975 | Zygraich et al. |
| 4,631,189 A | 12/1986 | Kendall et al. |
| 4,639,339 A | 1/1987 | Murashige et al. |
| 4,808,700 A | 2/1989 | Anderson et al. |
| 4,816,568 A | 3/1989 | Hamilton, Jr. et al. |
| 4,950,596 A | 8/1990 | Cheng et al. |
| 5,109,026 A | 4/1992 | Hoskinson et al. |
| 5,169,758 A | 12/1992 | Fischer et al. |
| 5,240,843 A | 8/1993 | Gibson et al. |
| 5,580,856 A | 12/1996 | Prestrelski et al. |
| 5,618,539 A | 4/1997 | Dorval et al. |
| 5,691,163 A | 11/1997 | Cameron et al. |
| 6,037,116 A | 3/2000 | Wiggins et al. |
| 6,127,181 A | 10/2000 | Kadkade |
| 6,194,136 B1 | 2/2001 | Livesey et al. |
| 6,248,588 B1 | 6/2001 | Crespo et al. |
| 6,689,600 B1 | 2/2004 | Wu et al. |
| 7,235,391 B2 | 6/2007 | Wu et al. |
| 9,101,607 B2 | 8/2015 | Drew et al. |
| 9,657,061 B2 | 5/2017 | Laidler et al. |
| 10,029,007 B2 | 7/2018 | Drew et al. |
| 10,086,064 B2 | 10/2018 | Drew |
| 10,206,960 B2 | 2/2019 | Drew et al. |
| 2004/0110267 A1 | 6/2004 | Sundar |
| 2004/0253574 A1 | 12/2004 | Schuler et al. |
| 2005/0048058 A1 | 3/2005 | Yamazaki et al. |
| 2005/0239705 A1 | 10/2005 | Dake et al. |
| 2006/0073182 A1 | 4/2006 | Wong et al. |
| 2006/0154858 A1 | 7/2006 | Mattson et al. |
| 2006/0228334 A1 | 10/2006 | Rosa-Calatrava et al. |
| 2006/0247167 A1 | 11/2006 | Schlein et al. |
| 2007/0253941 A1 | 11/2007 | Naidu et al. |

(Continued)

FOREIGN PATENT DOCUMENTS

| | | |
|---|---|---|
| CA | 2083407 C | 5/1993 |
| CN | 101450209 A | 6/2009 |

(Continued)

OTHER PUBLICATIONS

U.S. Appl. No. 13/637,828, Drew et al.
U.S. Appl. No. 13/637,913, Drew et al.
U.S. Appl. No. 14/349,481, Drew et al.
"Composition of Medium 199," XP002596423 (2009). Retrieved from the Internet: <URL:http://www.fishersci.com/wps/downloads/segment/Scientific/pdf/cmbrex_medium_199.pdf>.
"Renaturation (Molecular Biology)," <http://what-when-how.com/molecular-biology/renaturation-molecular-biology/>, retrieved on Nov. 15, 2015 (2 pages).
Abdul-Fattah et al., "Drying-induced variations in physicochemical properties of amorphous pharmaceuticals and their impact on Stability II: stability of a vaccine," Pharm Res. 24(4):715-27 (2007).

(Continued)

*Primary Examiner* — Barry A Chestnut
(74) *Attorney, Agent, or Firm* — Clark & Elbing LLP; Susan M. Michaud (57) ABSTRACT

The invention relates to an immunogenic composition comprising influenza virus antigens derived from at least 5 influenza virus strains and one or more compounds of formula (I) or physiologically acceptable salts or esters thereof: wherein: $R_1$ represents hydrogen or $C_{1-6}$ alkyl; $R_2$ represents $C_{1-6}$ alkyl; and $R_3$ represents $C_{1-6}$ alkyl. The invention also relates to methods of preparing the immunogenic composition, to pharmaceutical and vaccine compositions comprising the immunogenic composition and to use of the immunogenic, pharmaceutical and vaccine compositions for preventing influenza virus infection.

17 Claims, 1 Drawing Sheet

(56) References Cited

U.S. PATENT DOCUMENTS

| | | |
|---|---|---|
| 2008/0107631 A1 | 5/2008 | Wu et al. |
| 2008/0299168 A1 | 12/2008 | Dadey et al. |
| 2009/0123436 A1 | 5/2009 | Opperman |
| 2010/0029569 A1 | 2/2010 | Bjorn et al. |
| 2010/0260796 A1 | 10/2010 | Belin-Poput et al. |
| 2011/0081363 A1 | 4/2011 | Whitney et al. |
| 2013/0071431 A1 | 3/2013 | Drew et al. |
| 2013/0129685 A1 | 5/2013 | Drew et al. |
| 2013/0156797 A1 | 6/2013 | Drew et al. |
| 2013/0164296 A1 | 6/2013 | Drew et al. |
| 2014/0294757 A1 | 10/2014 | Drew et al. |
| 2015/0110820 A1 | 4/2015 | Laidler et al. |
| 2016/0317665 A1 | 11/2016 | Drew et al. |
| 2017/0021008 A1 | 1/2017 | Drew |
| 2019/0000961 A1 | 1/2019 | Drew |
| 2019/0111128 A1 | 4/2019 | Drew et al. |
| 2019/0307819 A1 | 10/2019 | Drew et al. |
| 2019/0350846 A1 | 11/2019 | Drew |

FOREIGN PATENT DOCUMENTS

| | | |
|---|---|---|
| CN | 101670104 A | 3/2010 |
| EP | 0130619 A2 | 1/1985 |
| EP | 0156242 A2 | 10/1985 |
| EP | 0312114 A2 | 4/1989 |
| EP | 0376361 A2 | 7/1990 |
| EP | 0890362 A1 | 1/1999 |
| EP | 1946776 A1 | 7/2008 |
| EP | 1961761 A1 | 8/2008 |
| EP | 1133316 B1 | 1/2009 |
| JP | 61189228 A | 8/1986 |
| JP | 2003-095956 A | 4/2003 |
| JP | 2003-261591 A | 9/2003 |
| WO | WO-89/11297 A1 | 11/1989 |
| WO | WO-90/05182 A1 | 5/1990 |
| WO | WO-93/00807 A1 | 1/1993 |
| WO | WO-94/04174 A1 | 3/1994 |
| WO | WO-95/10605 A1 | 4/1995 |
| WO | WO-95/11700 A1 | 5/1995 |
| WO | WO-97/04801 A1 | 2/1997 |
| WO | WO-97/15331 A1 | 5/1997 |
| WO | WO-99/27071 A1 | 6/1999 |
| WO | WO-00/29024 A1 | 5/2000 |
| WO | WO-01/29198 A1 | 4/2001 |
| WO | WO-01/93829 A2 | 12/2001 |
| WO | WO-02/101412 A2 | 12/2002 |
| WO | WO-03/035827 A2 | 5/2003 |
| WO | WO-2004/002534 A1 | 1/2004 |
| WO | WO-2004/007537 A2 | 1/2004 |
| WO | WO-2004/035818 A1 | 4/2004 |
| WO | WO-2004/105790 A1 | 12/2004 |
| WO | WO-2004/108753 A1 | 12/2004 |
| WO | WO-2005/042029 A2 | 5/2005 |
| WO | WO-2005/056808 A2 | 6/2005 |
| WO | WO-2005/062709 A2 | 7/2005 |
| WO | WO-2006/081587 A2 | 8/2006 |
| WO | WO-2006/085082 A1 | 8/2006 |
| WO | WO-2006/092668 A2 | 9/2006 |
| WO | WO-2006/094974 A2 | 9/2006 |
| WO | WO-2006/127150 A2 | 11/2006 |
| WO | WO-2007/035455 A2 | 3/2007 |
| WO | WO-2007/038926 A1 | 4/2007 |
| WO | WO-2007/056847 A1 | 5/2007 |
| WO | WO-2007/095337 A2 | 8/2007 |
| WO | WO-2007/138135 A1 | 12/2007 |
| WO | WO-2007/149287 A2 | 12/2007 |
| WO | WO-2008/051245 A2 | 5/2008 |
| WO | WO-2008/058035 A1 | 5/2008 |
| WO | WO-2008/114021 A1 | 9/2008 |
| WO | WO-2008/118691 A2 | 10/2008 |
| WO | WO-2008/150479 A2 | 12/2008 |
| WO | WO-2009/006097 A1 | 1/2009 |
| WO | WO-2009/015343 A2 | 1/2009 |
| WO | WO-2009/129101 A1 | 10/2009 |
| WO | WO-2010/035001 A1 | 4/2010 |
| WO | WO-2010/146598 A2 | 12/2010 |
| WO | WO-2011/109415 A2 | 9/2011 |
| WO | WO-2011/121301 A1 | 10/2011 |
| WO | WO-2011/121305 A2 | 10/2011 |
| WO | WO-2011/121306 A1 | 10/2011 |
| WO | WO-2013/050780 A1 | 4/2013 |
| WO | WO-2013/131898 A1 | 9/2013 |
| WO | WO-2015/155527 A1 | 10/2015 |
| WO | WO2015155527 | * 10/2015 |
| WO | WO-2018/206930 A1 | 11/2018 |

OTHER PUBLICATIONS

Abdul-Fattah et al., "The effect of annealing on the stability of amorphous solids: chemical stability of freeze-dried moxalactam," J Pharm Sci. 96(5):1237-50 (2007).

Andersson et al., "Protein stabilising effect of polyethyleneimine" J Biotech. 72(1-2):21-31 (1999).

Andersson et al., "Stabilizing effect of chemical additives against oxidation of lactate dehydrogenase," Biotechnol Appl Biochem. 32:145-53 (2000).

Arakawa et al., "Factors affecting short-term and long-term stabilities of proteins," Adv Drug Deliv Rev. 10:1-28 (1993).

Arakawa et al., "Factors affecting short-term and long-term stabilities of proteins," Adv Drug Deliv Rev. 46(1-3):307-26 (2001).

Bandell et al., "Protective Efficacy of Live-Attenuated Influenza Vaccine (Multivalent, Ann Arbor Strain): A Literature Review Addressing Interference," Expert Rev Vaccines. 10(8):1131-1141 (2011).

Beech et al., "Effect of dimethylglycine on antibody response to influenza vaccination in horses," J Equine Vet Sci. 7(2):62-65 (1987).

Berge et al., "Preservation of enteroviruses by freeze-drying," Appl Microbiol. 22(5):850-3 (1971).

Braun et al., "Development of a freeze-stable formulation for vaccines containing aluminum salt adjuvants," Vaccine. 27(1):72-9 (2009).

Breteler, "The MSM Miracle," available <http://www.msm-info.com/>, Jul. 2001 (12 pages).

Brody et. al., "Studies on antigenic competition. II. Evidence for effect at level of antigen 'processing'," Immunology 22(1):75-85 (1972).

Brown et al., "Assembly of hybrid bacteriophage Qbeta virus-like particles," Biochemistry. 48(47):11155-7 (2009).

Bryjak et al., "Storage stabilization and purification of enzyme by water-soluble synthetic polymers," Enzyme Microb Technol. 16:616-21 (1994).

Bryjak, "Storage stabilization of enzyme activity by poly(ethyleneimine)," Bioprocess Eng. 13:177-81 (1995).

Burke et al., "Formulation, stability, and delivery of live attenuated vaccines for human use," Crit Rev Ther Drug Carrier Syst. 16(1):1-83 (1999).

Carpenter et al., "The mechanism of cryoprotection of proteins by solutes," Cryobiology. 25(3):244-55 (1988).

Chang et al., "Mechanisms of protein stabilization in the solid state," J Pharm Sci. 98(9):2886-908 (2009).

Chen et al., "Stabilization of recombinant human keratinocyte growth factor by osmolytes and salts," J Pharm Sci. 85(4):419-22 (1996).

Cleland et al., "Glycine betaine as a cryoprotectant for prokaryotes," J Microbiol Methods. 58(1):31-8 (2004).

Cosquer et al., "Nanomolar levels of dimethylsulfoniopropionate, dimethylsulfonioacetate, and glycine betaine are sufficient to confer osmoprotection to *Escherichia coli*," Appl Environ Microbiol. 65(8):3304-11 (1999).

Costantino et al., "Effect of excipients on the stability and structure of lyophilized recombinant human growth hormone," J Pharma Sci. 87(11):1412-20 (1998).

Davidson et al. "Effect of sucrose/raffinose mass ratios on the stability of co-lyophilized protein during storage above the Tg" Pharm Res. 18(4):474-9 (2001).

Drew et al., "Stable vaccine technology," displayed in Vienna Oct. 3-5, 2010.

(56) References Cited

OTHER PUBLICATIONS

Foreman et al., "Effects of charged water-soluble polymers on the stability and activity of yeast alcohol dehydrogenase and subtilisin Carlsberg," Biotechnol Bioeng. 76(3):241-6 (2001).
Greiff et al., "Effects of freezing, storage at low temperatures, and drying by sublimation in vacuo on the activities of measles virus," Nature. 202:624-5 (1964).
Gupta et al., "Stabilization of respiratory syncytial virus (RSV) against thermal inactivation and freeze-thaw cycles for development and control of RSV vaccines and immune globulin," Vaccine. 14(15):1417-20 (1996).
Holtmann et al., "Thermoprotection of Bacillus subtilis by exogenously provided glycine betaine and structurally related compatible solutes: involvement of Opu transporters," J Bacteriol. 186(6):1683-93 (2004).
Hubálek, "Protectants used in the cryopreservation of microorganisms," Cryobiology. 46(3):205-29 (2003).
International Search Report and Written Opinion for International Application No. PCT/GB2018/051226, dated Jul. 10, 2018 (15 pages).
Ishimaru et al., "Pressure-inactivated FMDV: a potential vaccine," Vaccine. 22(17-18):2334-9 (2004).
Izutsu et al., "Stabilization of protein structure in freeze-dried amorphous organic acid buffer salts," Chem Pharm Bull (Tokyo). 57(11):1231-6 (2009).
Izutsu, "Stabilization of therapeutic proteins by chemical and physical methods" in *Therapeutic Proteins, Smales and James* ed. Humana Press ISBN 1-58829-390-4, 287-292 (2005) (8 pages).
Kim et al., "Counteracting effects of renal solutes on amyloid fibril formation by immunoglobulin light chains," J Biol Chem. 276(2):1626-33 (2001).
Land et al., "The Challenges of Antimicrobial Preservation of a Sugar-free Liquid Risedronate Sodium Formulation for US and EMEA Pediatric Use," Post No. M1187. Procter & Gamble Pharmaceuticals, 2009 AAPS Natual Meeting and Exposition, Los Angeles, CA (2009).
Larski et al., "Stabilization of Newcastle disease virus by dimethyl sulfoxide," Acta Virol. 16(4):349-52 (1972).
Lever et al., "Using high-performance liquid chromatography to measure the effects of protein-stabilizing cosolvents on a model protein and fluorescent probes," Anal Biochem. 367(1):122-33 (2007).
Liao et al., "Influence of the active pharmaceutical ingredient concentration on the physical state of mannitol—implications in freeze-drying," Pharm Res. 22(11):1978-85 (2005). Abstract provided.
Liao et al., "Protective mechanism of stabilizing excipients against dehydration in the freeze-drying of proteins," Pharm Res. 19(12):1854-61(2002).
Lloyd et al., "A comparison of glycine, sarcosine, N,N-dimethylglycine, glycinebetaine and N-modified betaines as liposome cryoprotectants" J Pharm Pharmacol. 44(6):507-11 (1992).
Maltesen et al., "Drying methods for protein pharmaceuticals," Drug Disc Today Technol. 5(2-3):e81-8 (2008).
Manual of Policies and Procedures, Center for Drug Evaluation and Research, "Applications for Parenteral Products in Plastic Immediate Containers," MAPP 6020.2 (2007).
Mateu, "Assembly, stability and dynamics of virus capsids," Arch Biochem Biophys. 531(1-2):65-79 (2013).
McGann et al., "Cryoprotection by dimethyl sulfoxide and dimethyl sulfone," Cryobiology. 24(1):11-6 (1987).
Michaelis et al., "Dimethylglycine buffer," J Biol Chem. 115:221-2 (1936).
Nishiguchi et al., "Temperature- and concentration-dependence of compatibility of the organic osmolyte beta-dimethylsulfoniopropionate," Cryobiology. 29(1):118-24 (1992).
Paleg et al., "Proline and glycine betaine influence protein solvation," Plant Physiol. 75(4):974-8 (1984).
Pebody et al., "Low Effectiveness of Seasonal Influenza Vaccine in Preventing Laboratory-Confirmed Influenza in Primary Care in the United Kingdom: 2014/15 Mid-Season Results," Euro Surveil 20(5):21025 (2015) (7 pages).
Peek et al., "A rapid, three-step process for the preformulation of a recombinant ricin toxin A-chain vaccine," J Pharm Sci. 96(1):44-60 (2007).
Pikal et al., "The effects of formulation variables on the stability of freeze-dried human growth hormone," Pharm Res. 8(4):427-36 (1991).
Popova et al., "Cryoprotective effect of glycine betaine and glycerol is not based on a single mechanism," Cryo Letters. 22(5):293-8 (2001).
Publication by Lymphomation.org, <http://www.lymphomation.org/side-effect-HAMA.htm>, accessed Dec. 2, 2017 (2 pages).
Rathore et al., "Current perspectives on stability of protein drug products during formulation, fill and finish operations." Biotechnol Prog. 24(3):504-14 (2008).
Reap et al., "Stimulation of the immune response by dimethylglycine, a nontoxic metabolite," J Lab Clin Med. 115(4):481-6 (1990).
Reichert et al., "Development trends for monoclonal antibody cancer therapeutics," Nat Rev Drug Discov. 6(5):349-56 (2007).
Roy et al., "Freeze-drying of proteins: some emerging concerns," Biotechnol Appl Biochem. 39(Pt 2):165-77 (2004).
Santoro et al., "Increased thermal stability of proteins in the presence of naturally occurring osmolytes," Biochemistry. 31(23):5278-83 (1992).
Schiefner et al., "Structural basis for the binding of compatible solutes by ProX from the hyperthermophilic archaeon Archaeoglobus fulgidus," J Biol Chem. 279(46):48270-81 (2004).
Search Report under Section 17(5) for Great Britain Application No. GB1707367.7, dated Feb. 28, 2018 (5 pages).
Sigalov, "Cryopreservation and long-term storage of human low density lipoproteins," Eur J Clin Chem Clin Biochem. 33(2):73-80 (1995).
Singh et al., "The osmoprotectants glycine and its methyl derivatives prevent the thermal inactivation of protective antigen of Bacillus anthracis," Biochem Biophys Res Comm. 316(2):559-64 (2004).
Sjölander et al., "ISCOMs: an adjuvant with multiple functions," J Leukoc Biol. 64(6):713-23 (1998).
Skountzou et al., "Influenza Virus-Specific Neutralizing IgM Antibodies Persist for a Lifetime," Clin Vaccine Immunol. 21(11):1481-1489 (2014).
Stabilitech: "Innovations in Health," dated Nov. 19, 2009 (21 pages).
Suntanto et al., "Home delivery of heat-stable vaccines in Indonesia: outreach immunization with a prefilled single-use injection device" Bull World Health Organ. 77(2):119-26 (1999).
Suzuki et al., "Mammalian lactoferrin receptors: structure and function," Cell Mol Life Sci. 62(22):2560-75 (2005).
Tang et al., "Measurement of the kinetics of protein unfolding in viscous systems and implications for protein stability in freeze-drying," Pharm Res. 22(7):1176-85 (2005).
Tang et al., "The effect of stabilizers and denaturants on the cold denaturation temperatures of proteins and implications for freeze-drying," Pharm Res. 22(7):1167-75 (2005).
Tesconi et al., "Freeze-drying above room temperature," J Pharm Sci. 88(5):501-6 (1999).
The class notes from Indiana University on viral structure, http://courses.bio.indiana.edu/M430-Taylor/structure.html, retrieved on Apr. 13, 2015 (5 pages).
Tiyaboonchai et al., "Insulin containing polyethylenimine-dextran sulfate nanoparticles," Int J Pharm. 255(1-2):139-51 (2003).
Vasudevamurthy et al., "Enzyme stabilization using synthetic compensatory solutes" Biocat and Biotransform. 23(3/4):285-91 (2005).
Wallis et al., "Stabilization of enveloped viruses by dimethyl sulfoxide," J Virol. 2(9):953-4 (1968).
Wolff et al., "Comparative stability study of lyophilised aluminium hydroxide adjuvanted vaccine formulations containing a monoclonal antibody as a model antigen and methods used for their characterisation," Colloids and Surfaces A: Physicochem. Eng Aspects. 339:82-93 (2009).

(56) References Cited

OTHER PUBLICATIONS

Wolff et al., "Protection of aluminum hydroxide during lyophilisation as an adjuvant for freeze-dried vaccines," Colloids and Surfaces A: Physicochem. Eng Aspects. 330:116-26 (2008).
Wolff et al., "Development of a formulation protecting aluminum hydroxide adjuvanted vaccines during lyophilisation," 6th World Meeting on Pharmaceutics, Biopharmaceutics and Pharmaceutical Technology, Barcelona, Apr. 7-10, 2008.
Yancey, "Organic osmolytes as compatible, metabolic and counteracting cytoprotectants in high osmolarity and other stresses," J Exp Biol. 208:2819-30 (2005).

* cited by examiner

VACCINE COMPOSITIONS

FIELD OF THE INVENTION

The invention relates to an immunogenic composition which comprises influenza viral antigens derived from at least 5 strains of influenza virus and specific dialkylglycine and trialkylglycine compounds. The invention also relates to methods of preparing the immunogenic composition, to pharmaceutical and vaccine compositions comprising the immunogenic composition and to use of the immunogenic, pharmaceutical and vaccine compositions for preventing influenza virus infection.

BACKGROUND OF THE INVENTION

Influenza virus is a member of the Orthomyxoviridae family. There are four types of influenza viruses designated A, B, C and D. A, B and C infect humans.

Seasonal epidemics of influenza can spread around the world quickly and inflict a significant economic burden in terms of hospital and other healthcare costs and lost productivity. The World Health Organization estimates that in annual influenza epidemics there are between three and five million cases of severe illness and approximately 250,000 and 500,000 deaths every year around the world.

The current seasonal influenza vaccines are trivalent or quadrivalent. The cost of the vaccines was 3.1 billion US dollars in 2015 and it is forecast to be 4.3 billion dollars by 2025. Each year new seasonal influenza vaccines are developed based on predicting what will be the predominant circulating influenza strains.

An influenza pandemic occurs when a new influenza strain emerges in the population with high pathogenicity and antigenic novelty. Global pandemics can afflict between 20% and 40% of the world's population in a single year. The pandemic of 1918-19, for example, affected 200 million people, killing over 30 million worldwide. Although healthcare has dramatically improved since that time, with vaccines and antiviral therapies being developed, it is estimated that a pandemic today would result in two to seven million deaths globally.

The number of antigens that a vaccine can comprise was thought to be limited because of immune interference (J Exp Med. 1969 Oct. 1; 130(4): 821-832). When more antigens are included in a composition, the response to each antigen is reduced, thus limiting the number of antigens which could be included in a vaccine. Influenza vaccines are typically trivalent and more recently quadrivalent.

SUMMARY OF THE INVENTION

Surprisingly, the present inventors have found that a multivalent immunogenic composition can be prepared comprising antigens from 5 or more strains of influenza virus. The immunogenic composition is prepared by freezing, freeze-drying or heat-treating the influenza virus antigens in the presence of dialkylglycines and trialkylglycines such as dimethylglycine (DMG) and/or trimethylglycine (TMG).

Developing an immunogenic composition comprising antigens from at least 5 influenza virus strains was unexpected owing to immune interference. Previous attempts at putting more influenza virus strains into a single vaccine have failed because of the amount of antigen needed. The inventors have surprisingly developed an immunogenic composition comprising influenza virus antigens from 15 strains of influenza virus by heat-treating the influenza virus antigens in the presence of DMG and TMG. The developed composition is surprisingly expected to confer protection against all the influenza strains from which the influenza virus antigens in the composition are derived.

Current influenza vaccines are trivalent or quadrivalent, i.e. they are limited to containing antigens from 3 or 4 influenza strains. Each year, the seasonal influenza vaccine has to be redesigned based on what is predicted to be the predominant circulating influenza strains of that season, which has proven an inexact science with strain selection mismatches in 6 out of 12 years (between 2003/04 to 2014/15)—a recent example being the H3N2 strain selection in 2014/15 for the northern hemisphere was A/Texas/50/2012, however A/Switzerland/9715293/2013 was eventually dominant resulting in vaccine efficacy as low as 3.4% (Pebody R G, et al (2015) LOW EFFECTIVENESS OF SEASONAL INFLUENZA VACCINE IN PREVENTING LABORATORY-CONFIRMED INFLUENZA IN PRIMARY CARE IN THE UNITED KINGDOM: 2014/15 MID-SEASON RESULTS. Eurosurveillance, Volume 20, Issue 5; http://www.eurosurveillance.org/ViewArticle.aspx?ArticleId=21025). Providing a vaccine comprising antigens from 5 or more influenza strains would not only increase the strain coverage thereby including strains that, when the strain selections are made, are not the most prevalent but have the potential to dominate, it could also reduce the frequency at which the seasonal influenza vaccine has to be redesigned. Furthermore, it has the potential to provide an influenza vaccine against all strains of types A, B, C and D, inclusive of all subtypes together with antigenic drift variants. This may eliminate the requirement for annually redesigning the seasonal influenza vaccine.

The invention therefore provides an immunogenic composition comprising influenza virus antigens derived from at least 5 influenza virus strains and one or more compounds of formula (I) or physiologically acceptable salts or esters thereof:

$$\begin{array}{c} R_1 \\ \diagdown \\ N^{\oplus} \diagup \diagdown \diagup O \\ R_2 \diagup \diagup \diagdown \\ R_3 \quad O^{\ominus} \end{array} \quad (I)$$

wherein:
$R_1$ represents hydrogen or $C_{1-6}$ alkyl;
$R_2$ represents $C_{1-6}$ alkyl; and
$R_3$ represents $C_{1-6}$ alkyl.

The invention also provides a method of preparing the immunogenic composition according to the invention, said method comprising (a) freezing, (b) heat-treating, and/or (c) freeze-drying (i) a single aqueous composition which comprises the influenza virus antigens and the compound(s), or (ii) two or more aqueous compositions, each of which comprises at least one influenza virus antigen and at least one compound(s), and subsequently combining the resulting treated compositions.

The invention also provides an immunogenic composition which is obtained or obtainable by the method of the invention.

The invention also provides a pharmaceutical composition comprising the immunogenic composition of the invention and, optionally, a pharmaceutically acceptable excipient, carrier or diluent.

The invention also provides a vaccine composition comprising the immunogenic composition of the invention and, optionally, a pharmaceutically acceptable excipient, carrier or diluent.

The invention also provides a method of inducing an immune response against an influenza virus in a subject, which method comprises administering to the subject the immunogenic composition of the invention, the pharmaceutical composition of the invention, or the vaccine composition of the invention.

The invention also provides a method of preventing an influenza virus in a subject, which method comprises administering to the subject the immunogenic composition of the invention, the pharmaceutical composition of the invention, or the vaccine composition of the invention.

The invention also provides the immunogenic composition of the invention, the pharmaceutical composition of the invention, or the vaccine composition of the invention for use in inducing an immune response against an influenza virus in a subject.

The invention also provides the immunogenic composition of the invention, the pharmaceutical composition of the invention, or the vaccine composition of the invention for use in preventing an influenza virus infection in a subject.

The invention also provides use of the immunogenic composition of the invention, the pharmaceutical composition of the invention, or the vaccine composition of the invention in the manufacture of a medicament for inducing an immune response against an influenza virus in a subject.

The invention also provides use of the immunogenic composition of the invention, the pharmaceutical composition of the invention, or the vaccine composition of the invention in the manufacture of a medicament for preventing an influenza virus infection in a subject.

The invention also provides a unit dosage form comprising the immunogenic composition of the invention, the pharmaceutical composition of the invention, or the vaccine composition of the invention.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting. Unless defined otherwise, technical and scientific terms used herein have the same meaning as commonly understood by a person skilled in the art to which this invention belongs.

In addition, as used in this specification and the appended claims, the singular forms "a", "an", and "the" include plural referents unless the content clearly dictates otherwise. Thus, for example, reference to "a compound" includes two or more instances or versions of such compounds, or reference to "a strain" includes two or more such strains, and the like.

In general the term "comprising" is intended to mean including but not limited to, for example a composition "comprising an influenza antigen" indicates that the composition has that influenza antigen, but may comprise additional influenza antigens. In some embodiments of the invention, the word "comprising" can be replaced by the word "consisting essentially of".

All publications, patents and patent applications cited herein, whether supra or infra, are hereby incorporated by reference in their entirety.

The Immunogenic, Pharmaceutical and Vaccine Compositions

The immunogenic composition of the invention comprises influenza virus antigens derived from at least 5 influenza virus strains. The pharmaceutical composition of the invention comprises the immunogenic composition of the invention. The pharmaceutical composition can optionally comprise a pharmaceutically acceptable excipient, carrier or diluent. The vaccine composition of the invention comprises the immunogenic composition of the invention. The vaccine composition can optionally comprise a pharmaceutically acceptable excipient, carrier or diluent.

By describing a composition as "immunogenic" means the composition must be able to induce immune responses. For example, the immunogenic, pharmaceutical or vaccine composition is a composition that, when administered to a patient such as a human patient, may cause the generation of an immune response. Preferably the immune response is directed against an influenza virus. More preferably, the immune response is directed against at least one of the influenza virus strains from which one of the antigens in the composition is derived. Even more preferably the immune response is direct against all of the influenza virus strains from which the influenza virus antigens in the composition are derived. In one embodiment, the immunogenic, pharmaceutical or vaccine composition comprises an effective amount of the influenza virus antigens. An effective amount of the influenza virus antigens is an amount sufficient to induce an immune response when it is administered to a patient as part of the immunogenic composition. The effective amount may vary depending on a number of factors including the size of the patient, their age and whether they are immunocompromised. There may need to be multiple (e.g. 2, 3, or more) administrations to induce protection immunity.

The immune response may be a T cell response. The immune response may be a B cell response. The immune response may be both a T cell and B cell response. For example, the immune responses include B cell (humoral) responses, in which antibodies specific for influenza virus antigens are produced by differentiated B lymphocytes, and/or T cell (cell mediated) responses, in which various types of T lymphocytes respond to influenza virus antigens. When the immunogenic, pharmaceutical or vaccine composition is administered to a subject, the subject may produce antibodies. The antibodies are preferably specific for one or more or all of the influenza virus strains which the influenza virus antigens are derived from. The immune responses may result in seroconversion in a subject, i.e. a level in the subject which would produce antibodies in response to exposure to the influenza virus antigens in the future, e.g., at a point in time from 2 days to 20 years from administration, such as 1, 3 or 6 months, or 1, 2, 5, or 10 years. A person skilled in the art can determine if a subject is seroconverted using techniques known in the art, for example, taking blood samples from the subject and testing for the levels of antibody.

Methods of determining whether a composition can induce immune responses are well known to a person skilled in the art. For example, using a HAI assay (e.g. see the Example). Methods of measuring humoral and cellular immunity include ELISA, cytotoxic T-lymphocyte (CTL) assay, CTL precursor frequency assay, T-cell proliferation assays, carboxyfluorescein diacetate succinimidyl ester assays, intracellular and extracellular cytokine or antibody production by cells in culture using either ELISA or multiplex and flow cytometry, polyfunctional T-cell assays, ELISpot both cytokine recall and ASC (antigen-specific antibody-secreting cells), MHC class I/II tetramers binding, HAI, NAI, virus neutralisation, and DTH.

Preferably the immune response is protective, i.e. if the immunogenic, pharmaceutical or vaccine composition is administered to the host that host develops a protective immune response to an influenza virus. Typically the protective immune response is against at least one of the influenza virus strains from which at least one of the antigens in the composition is derived, and preferably against all of the influenza virus strains from which the antigens in the immunogenic composition are derived. Whether an immunogenic, pharmaceutical or vaccine composition is protective may be determined via a challenge assay. For example, the immunogenic, pharmaceutical or vaccine composition may be administered to a test animal such as a mouse, and then the mouse may be exposed to an influenza virus, preferably one of the strains from which the antigen in the composition is derived. If the mouse survives infection by the influenza for at least 2, at least 3, at least 5, at least 7, at least 14 or at least 21 days, the immunogenic, pharmaceutical or vaccine composition is considered to be able to induce a protective immune response. Alternatively, a haemmagglutination inhibition (HAI) assay is a standard technique which can be used to indicate whether a composition can induce a protective immune response. An exemplary protocol for this assay is set out in the Example herein. HAI titres equal to or greater than 40 post background correction are considered to indicate a protective immunity response level (Skountzou, Ioanna et al. "Influenza Virus-Specific Neutralizing IgM Antibodies Persist for a Lifetime." Ed. S. A. Plotkin. Clinical and Vaccine Immunology: CVI 21.11 (2014): 1481-1489. PMC.). The background can be corrected by deducting the pre-administration HAI titre, for example, deducting the HAI titre recorded 7 days prior to administration. Thus in some embodiments an effective amount of the influenza antigens can be an amount which results in an HAI titre of 40 or more post background correction against one or more of the influenza virus strains that the influenza virus antigens are derived from.

As discussed herein, the immunogenic composition may raise immune responses against influenza virus strains from which the influenza virus antigens in the immunogenic composition have not been derived. Such immune responses are preferably in addition to raising immune responses to one or more, preferably all, of the influenza strains from which the influenza virus antigens are derived. This cross-reactivity is an advantage as it can protect against influenza virus strains from which the influenza virus antigens in the immunogenic composition have not been derived. Therefore protection can be gained against an influenza virus strain which has mutated because of antigenic drift. The immune response raised following the administration of the immunogenic, pharmaceutical or vaccine composition may be against one or more strains and/or one or more subtypes from which the antigens present in the composition have not been derived. In some embodiments an effective amount of the influenza virus antigens can be an amount which results in an HAI titre of 40 or more post background correction against one or more influenza virus strains from which the influenza virus antigens in the immunogenic composition have not been derived. In such embodiments, preferably the effective amount also results in an HAI titre of 40 or more post background correction against one or more, preferably all, the influenza virus strains from which the influenza virus antigens in the immunogenic composition have been derived. The immunogenic, pharmaceutical or vaccine composition may raise an immune response against any influenza virus strain, such as those described herein. The influenza virus strain may be a seasonal strain or a pandemic strain. The immunogenic, pharmaceutical or vaccine composition may raise an immune response against all strains of types A, B, C and D inclusive of all subtypes together with antigenic drift variants. The immunogenic, pharmaceutical or vaccine composition may raise an immune response against all subtypes of influenza A and/or all subtypes of influenza B. The immunogenic, pharmaceutical or vaccine composition may raise an immune response against all strains of influenza A and/or all strains of influenza B. The requirement for annually redesigning the seasonal influenza vaccine may be eliminated.

The immune responses discussed herein may occur when the immunogenic, pharmaceutical or vaccine composition of the invention is administered to a subject. For example, the immunogenic, pharmaceutical or vaccine composition of the invention when administered to a subject may induce an immune response against at least one of the at least 5 influenza virus antigens. Preferably the immune response is against all five influenza virus antigens. The immune response is preferably against all of the influenza virus antigens present in the immunogenic composition, such as 15. The immune response is preferably protective. As discussed herein, HAI titres equal to or greater than 40 post background correction are considered to indicate a protective immunity response level. Thus in some embodiments the immunogenic, pharmaceutical or vaccine composition of the invention when administered to a subject can result in an HAI titre of 40 or more post background correction for one or more or each of the influenza viral strains from which the influenza virus antigens are derived. In some embodiments the immunogenic, pharmaceutical or vaccine composition of the invention when administered to a subject can result in an HAI titre of 40 or more post background correction for one or more influenza virus strains from which the influenza virus antigens in the immunogenic composition have not been derived.

The immunogenic, pharmaceutical or vaccine composition of the invention when administered to a subject may induce seroconversion for at least one of the at least 5 influenza virus antigens. Preferably the seroconversion is for all five influenza virus antigens. The seroconversion is preferably for all of the influenza virus antigens present in the immunogenic composition, such as 15. A person skilled in the art could determine by known methods whether a subject, such as a human, is seroconverted. In some embodiments the immunogenic, pharmaceutical or vaccine composition of the invention can induce seroconversion for one or more or each of the influenza viral strains from which the influenza virus antigens are derived. In some embodiments the immunogenic, pharmaceutical or vaccine composition of the invention can induce seroconversion for one or more influenza virus strains from which the influenza virus antigens in the immunogenic composition have not been derived.

In some embodiments the immunogenic composition of the invention may consist essentially of influenza antigens derived from at least 5 strains and one or more compounds of formula (I) or physiologically acceptable salts or esters. In some embodiments the immunogenic composition of the invention may consist essentially of influenza antigens derived from at least 5 strains, one or more compounds of formula (I) or physiologically acceptable salts or esters and an adjuvant. In such embodiments, the immunogenic composition may comprise other components which do not materially affect the essential characteristics of the immunogenic composition.

Determining a pharmaceutically acceptable excipient, carrier or diluent is standard in the art. Numerous pharmaceutically acceptable excipients, carriers or diluents are well known and can readily be adapted for use in the present invention by those of skilled in this art. For example, suitable pharmaceutical acceptable excipients include carbohydrates, polyalcohols, amino acids, aluminium hydroxide, magnesium hydroxide, hydroxyapatite, talc, titanium oxide, iron hydroxide, magnesium stearate, carboxymethylcellulose, hydroxypropylmethylcellulose, microcrystalline cellulose, gelatin, vegetal peptone, xanthan, Arabic gum, or cyclodextrin. The pharmaceutical composition or vaccine composition may comprise or be a cream, emulsion, gel liposome, nanoparticle or ointment. Optionally the pharmaceutically acceptable excipient, carrier or diluent does not comprise any animal derived components.

Following freezing, freeze-drying, or heat-treating, the resulting composition can be thawed, reconstituted or cooled respectively, and then used as an immunogenic, pharmaceutical or vaccine composition. In one embodiment, the aqueous composition(s) described herein may comprise the pharmaceutically acceptable excipient, carrier or diluent. In such an embodiment, typically, the treatment is freezing or heat-treating. When the treatment is freeze-drying, the resulting composition may be reconstituted using a pharmaceutically acceptable excipient, carrier or diluent. The immunogenic, pharmaceutical or vaccine composition can be diluted as necessary with, for example, phosphate-buffered saline or Water for Injection, prior to use.

At least one of the influenza virus antigens are treated in accordance with the preparation method of the invention, i.e. freezing, heat-treating and/or freeze-drying the aqueous composition(s) comprising the influenza virus antigens and compound(s) of the invention. Preferably all of the influenza virus antigens in the immunogenic, pharmaceutical or vaccine composition are treated in accordance with the preparation method of the invention. One or more of the influenza virus antigens may be treated using a different treatment than one or more other influenza virus antigens. For example, one or more of the influenza virus antigens may be heat-treated and one or more other influenza virus antigens may be frozen.

The immunogenic, pharmaceutical or vaccine composition of the invention may be lyophilised. In such lyophilised embodiments the immunogenic, pharmaceutical or vaccine composition of the invention may comprise a stabiliser such as trehalose, lactose or maltose.

The immunogenic, pharmaceutical or vaccine composition may further comprise an adjuvant. An adjuvant is a compound which is used as an immunostimulant, i.e. enhances the host's immune response to an influenza virus. Suitable adjuvants include those described herein, including aluminium salt hydroxide.

In some embodiments the immunogenic, pharmaceutical or vaccine composition of the invention is administered to a patient, and this may induce an immune response in the patient. The types of immune response may be any of the immune responses described herein. Preferably, the immune response is directed against at least one of the influenza virus strains from which the antigen in the composition is derived. More preferably the immune response is directed against all of the influenza strains from which the antigens in the composition are derived. Preferably the immune response is protective. Methods of determining whether a composition can induce immune responses are well known to a person skilled in the art and examples are discussed herein.

The invention provides the immunogenic, pharmaceutical or vaccine composition of the invention for use in the prevention of influenza virus infection in a subject. The invention also provides a method of preventing an influenza virus infection comprising administering to a subject the immunogenic, pharmaceutical or vaccine composition of the invention. The method of preventing an influenza virus infection may comprise administering an effective amount of the immunogenic, pharmaceutical or vaccine composition of the invention to the subject. The invention also provides use of the immunogenic, pharmaceutical or vaccine composition of the invention in the manufacture of a medicament for the prevention of an influenza virus infection in a subject. The influenza virus infection prevented is typically at least one of the influenza virus strains from which at least one of the antigens in the composition is derived, and preferably all of the influenza virus strains from which the antigens in the composition are derived. The influenza virus infection prevented may be any influenza strain, such as those described herein. The influenza virus strain may be a seasonal strain or a pandemic strain. The immunogenic, pharmaceutical or vaccine composition may be administered in two doses. In such embodiments an effective amount is an amount that is sufficient to induce an immune response after a second dose is administered. Similarly a three dose regimen, or a regimen using a higher number of doses may be used.

The invention provides an immunogenic, pharmaceutical or vaccine composition for use in the vaccination of a subject against an influenza virus infection. The invention also provides a method of vaccination against an influenza virus infection comprising administering to a subject the immunogenic, pharmaceutical or vaccine composition of the invention. The method of vaccination may comprise administering an effective amount of the immunogenic, pharmaceutical or vaccine composition of the invention to the subject. The invention also provides use of the immunogenic, pharmaceutical or vaccine composition of the invention in the manufacture of a medicament for the vaccination against an influenza virus infection in a subject. The influenza virus vaccinated against is typically at least one of the influenza virus strains from which at least one of the antigens in the composition is derived, and preferably all of the influenza virus strains from which the antigens in the composition are derived. The influenza virus infection vaccinated against may be any influenza strain, such as those described herein. The influenza virus strain may be a seasonal strain or a pandemic strain.

A person skilled in the art can readily determine an appropriate amount of the pharmaceutical or vaccine composition to administer to a subject using known techniques.

The invention also provides a unit dosage form comprising the immunogenic, pharmaceutical or vaccine composition of the invention. The unit dosage form comprises a defined quantity of the influenza virus antigens and compound(s) which forms a dose of the immunogenic, pharmaceutical or vaccine composition. A skilled person could readily determine the defined quantity using techniques known in the art. The defined quantity is an amount which produces the desired immune response, such as the effective amount as described herein. The immune response may be any of those described herein. The immune response is preferably protective. As described herein, there may be more than one dose. Therefore the same number of unit dosage forms as there are number of doses in the dosage regimen may result in an immune response, which is preferably protective. Methods of determining whether a composition can induce immune responses are well known to a person skilled in the art and examples are discussed herein.

The immunogenic, pharmaceutical or vaccine composition can be administered by, for example, injection, to a human or animal patient. The patient may be in need of vaccination. Typically, the patient is a human. The immunogenic, pharmaceutical or vaccine composition may be administered by parenteral, enteral or topical administration. The immunogenic, pharmaceutical or vaccine composition may be administered as a spray (nasal, pulmonary), oral/suppository dosage or dermally. The immunogenic, pharmaceutical or vaccine composition may be administered subcutaneously.

The patient may be a human who is part of the "at-risk" population. Such patients include children, elderly patients and/or patients suffering from lung diseases, diabetes, cancer, or kidney or heart problems. This patient group is particularly preferred for treatment with the immunogenic, pharmaceutical or vaccine composition of the invention, because the immunity achieved with the present vaccines can be rapid when compared to standard vaccines and this reduces the risk of the patients being infected in the time period between vaccination and onset of immunity.

The terms "patient" and "subject" are used interchangeably herein. The terms do not denote a particular age and, thus, both adult and newborn individuals are intended to be covered. The terms "patient" and "subject" include humans and other primates, including non-human primates such as chimpanzees and other apes and monkey species. The terms "patient" and "subject" also include birds, including domestic, wild and game birds such as chickens, turkeys and other gallinaceous birds, ducks, and geese. The terms "patient" and "subject" also include farm animals such as cattle, sheep, pigs, goats and horses. The terms "patient" and "subject" also include domestic mammals such as dogs and cats. The terms "patient" and "subject" also include laboratory animals including rodents such as mice, rats and guinea pigs. Preferably the patient or subject is a human.

Influenza Virus Antigens

The immunogenic composition of the invention comprises influenza virus antigens derived from at least 5 influenza strains. The immunogenic composition may comprise influenza virus antigens derived from more than 5 influenza virus strains. The immunogenic composition may comprise influenza virus antigens derived from at least 6, at least 7, at least 8, at least 9, at least 10, at least 11, at least 12, at least 13, at least 14, or at least 15 influenza virus strains. The immunogenic composition preferably comprises influenza virus antigens derived from at least 6 or at least 7 influenza virus strains. The immunogenic composition may comprise influenza virus antigens derived from no more than 20 influenza virus strains. Thus the immunogenic composition may comprise influenza virus antigens derived from 5 to 20, 5 to 19, 5 to 18, 5 to 17, 5 to 16, or 5 to 15 influenza virus strains. The immunogenic composition may comprise influenza virus antigens derived from 6 to 20, 6 to 19, 6 to 18, 6 to 17, 6 to 16, or 6 to 15 influenza virus strains. The immunogenic composition may comprise influenza virus antigens derived from 7 to 15, 8 to 15, 8 to 15, 10 to 15, 11 to 15, 12 to 15, or 13 to 15 influenza virus strains. The immunogenic composition may comprise influenza virus antigens derived from 7 to 19, 9 to 18, 11 to 17, 13 to 16, 14 to 16, or 15 to 18 influenza virus strains.

The immunogenic composition preferably comprises influenza virus antigens derived from 15 influenza virus strains.

An antigen comprises at least one immunogenic epitope. The antigen may comprise one or more B cell epitope(s). The antigen may comprise one or more T cell epitope(s). The antigen may comprise one or more B cell epitope(s) and one or more T cell epitope(s). A skilled person can determine the presence of an immunogenic epitope using methods known in the art. The methods described herein for measuring immune responses could be used. For example, the presence of an immunogenic epitope may be determined using a HAI assay (e.g. see the Example). An antigen is able to induce an immune response, preferably in an animal, such as a human. For example, an antigen peptide sequence is a sequence which can induce such an immune response. Methods of determining whether such immune responses can be induced are well known to a person skilled in the art and particular examples are discussed herein.

An influenza virus antigen derived from an influenza virus strain may be all or part of that influenza viral strain. The influenza viral strain may be any influenza viral strain, such as those described herein. The influenza strain may be any type or subtype as described herein. A "whole influenza virus" is an influenza virus which comprises substantially all of the components of a wild type influenza virus.

An influenza virus antigen derived from an influenza virus strain may be an inactivated whole influenza virus, a split influenza virus, an influenza viral subunit, an influenza virosome or a live attenuated influenza virus of that influenza virus strain. The influenza virus antigens may all be prepared by the same technique. For example the influenza antigens may all be inactivated whole influenza viruses, split influenza viruses, influenza viral subunits, influenza virosomes or live attenuated influenza viruses. The influenza virus antigens may be prepared by more than one technique. For example, one or more of the influenza virus antigens may be inactivated whole influenza viruses and one or more of the influenza virus antigens may be subunit influenza viruses. An influenza virus antigen derived from an influenza virus strain may be prepared using cell culture (e.g. for an influenza viral subunit), or may be egg-derived (e.g. for an inactivated whole influenza virus). One or more of the influenza virus antigens may be prepared using cell culture and one or more of the influenza virus antigens may be egg-derived. An influenza virus antigen derived from an influenza virus strain may be prepared using Tobacco leaves, insect cells or virus-like particle (VLP) technology (Pillet et al; Vaccine; "Plant-derived H7 VLP vaccine elicits protective immune response against H7N9 influenza virus in mice and ferrets"; 2015 Nov. 17; 33(46):6282-9). Using cell culture is advantageous as (i) it does not require the use of chicken eggs which makes the influenza virus antigens safer for administering to egg allergy sufferers, and (ii) has the potential for faster start-up of an influenza vaccine manufacturing process since the process is not limited by egg supply capacity. The present invention has the advantage of being compatible with egg-derived and cell based manufacturing of vaccines.

A "live attenuated virus" is a virus which is less able to cause disease its host than a wild type virus. Thus a "live attenuated influenza virus" is less pathogenic to its host than a wild type influenza virus. The influenza virus may be attenuated by passaging the influenza virus through a foreign host, such as tissue culture or eggs. The virus may be passaged from 5 to 50 times, such as 20 or 30 times. An influenza virus antigen derived from an influenza virus strain may be a live attenuated influenza virus of that influenza virus strain.

Virus infectivity may be measured using a plaque assay. A suitable plaque forming assay involves infecting a confluent monolayer of host cells, suitably H9-derived neural stem cells or other primary undifferentiated neural cultures, or gliobastoma cells such as U251, at varying dilutions. A viral plaque is formed when a virus infects a cell within the fixed cell monolayer. The virus infected cell will lyse and spread the infection to adjacent cells and so on. The infected cell area will create plaques which can be seen visually or using a microscope, and these can be counted. If the number of plaques formed is greater than a reference virus, the test virus is more infectious that the reference virus.

Whole live attenuated virus can be useful as components of vaccine compositions as they comprise all of the components of a native virus. Since they comprise all of the components of a native virus, when a subject is immunised with a whole virus, they are exposed to numerous antigens which they may gain immunity to. An influenza virus antigen derived from an influenza virus strain may be a whole live attenuated influenza virus of that influenza virus strain.

An "inactivated virus" refers to a virus that has been inactivated by, for example, exposure of the virus to an agent that is capable of disrupting the viral coat. Such inactivated viruses are useful in vaccines as they contain viral antigens but are generally incapable of infecting the host. In some cases, however, an inactivated virus may not be fully inactivated, i.e. some particles of virus may remain after inactivation which are capable of infecting a host. An influenza virus antigen derived from an influenza virus strain may be am inactivated influenza virus of that influenza virus strain.

A "viral subunit" refers to a particle comprising a portion of a virus. For example a "viral subunit" may comprise a polynucleotide complexed with at least one viral coat protein, but not necessarily all of the viral coat proteins. A viral subunit is typically prepared using cell culture. The cells in the cell culture may be insect cells. The viral subunit may be a recombinant and/or purified. The viral subunit may be a recombinant and/or purified HA and NA. An influenza virus antigen derived from an influenza virus strain may be a viral subunit of that influenza virus strain, for example the HA and NA from that influenza virus strain.

A "split virus" is typically an inactivated virus which has been disrupted by detergents or other reagents to solubilise the lipid envelope. An influenza virus antigen derived from an influenza virus strain may be a split virus of that influenza virus strain.

An influenza virus antigen derived from an influenza virus strain may be an influenza protein, for example, any of the influenza virus proteins, such as surface proteins, described herein. In particular, an influenza virus antigen derived from an influenza virus strain may be a hemagglutinin (HA), neuraminidase (NA), nucleoprotein/nucleocapsid protein (NP), M1, M2, NS1, NS2(NEP), PA, PB1, PB1-F2 or PB2 protein. For example, an influenza virus antigen derived from an influenza virus strain may be HA1, HA2, HA3, HA4, HA5, HA6, HA7, HA8, HA9, HA10, HA11, HA12, HA13, HA14, HA15, HA16, HA17 or HA18. An influenza virus antigen derived from an influenza virus strain may be NA1, NA2, NA3, NA4, NA5, NA6, NA7, NA8 or NA9. For example, the influenza virus antigen derived from an influenza strain may be a HA or NA which is identical to the HA or NA from that influenza virus strain. An influenza virus antigen derived from an influenza virus strain may be a sequence which is identical to the sequence of an antigen present in that influenza virus strain. The influenza virus antigens derived from the influenza virus strains may comprise the same number of NA and HA proteins.

If an influenza virus antigen derived from an influenza virus strain is a protein, the influenza virus antigen is "derived from" the influenza virus strain if the sequence of the influenza virus antigen is at least 90% identical to the sequence of an antigen from that influenza virus strain. For example, the influenza virus antigen derived from an influenza virus strain may be a HA1 protein sequence which is at least 90% identical to the sequence of the HA1 protein present in a strain of influenza A which is subtype HA1, such as the H1N1 subtype of influenza A, e.g. 07/102 A/Solomon Islands/3/2006 (H1N1) (IVR-145). In a further example, the influenza virus antigen derived from an influenza virus strain may be a NA2 protein sequence which is at least 90% identical to the sequence of the NA2 protein present in a strain of influenza A which is subtype NA2, such as the H3N2 subtype of influenza type A, e.g. 09/310 A/Wisconsin/15/2009 (H3N2)(NYMCX-183). The sequence of an influenza virus antigen derived from an influenza virus strain may be at least 95%, at least 97%, at least 98%, at least 99% or 100% identical to the sequence of an antigen present in that influenza virus strain.

The antigen in the influenza virus strain from which the influenza virus antigen of the immunogenic composition of the invention is derived may be a fragment of a larger component, such as a protein, present in that influenza virus strain. For example, the fragment may be a portion of a HA. The fragment is able to induce an immune response in a subject, preferably a protective immune response. Thus the fragment comprises at least one immunogenic epitope. The fragment may comprise one or more B cell epitope(s). The fragment may comprise one or more T cell epitope(s). The fragment may comprise one or more B cell epitope(s) and one or more T cell epitope(s). A skilled person can determine the presence of an immunogenic epitope using methods known in the art. The methods described herein for measuring immune responses could be used. For example, the presence of an immunogenic epitope may be determined using a HAI assay (e.g. see the Example). If the fragment is protein, such as an influenza surface protein, the fragment is typically at least 50 amino acids in length. For example, the fragment may be at least 75, 100, 150, 200, 300, 400 or 500 amino acids in length. The fragment may be of any of the influenza proteins described herein. For example, the fragment may be a fragment of an NA or HA. If an influenza virus antigen derived from an influenza virus strain is a protein fragment, the influenza virus antigen is derived from the influenza virus strain if the sequence of the influenza virus antigen is at least 90% identical to the sequence of a fragment of protein present in that influenza virus strain. For example, the influenza virus antigen derived from an influenza virus strain may be a fragment of an NA1 protein sequence which is at least 90% identical to the sequence of the NA1 protein present in a strain of influenza A which is subtype NA1, such as the H1N1 subtype of influenza A, e.g. 08/100 A/Brisbane/59/2007 (IVR-148)(H1N1). The sequence of the influenza virus antigen derived from an influenza virus strain may be at least 95%, at least 97%, at least 98%, at least 99% or 100% identical to the sequence of a fragment of protein present in that influenza virus strain.

Methods of measuring sequence identity are well known in the art. When determining whether an influenza virus antigen sequence ("reference" sequence) is 90% identical to a sequence present in a particular influenza virus strain ("test" sequence), the test sequence is compared to the full length of the reference sequence. For example, when determining whether an influenza virus antigen of the invention is "derived from" a particular influenza virus strain, the "reference" sequence is the influenza virus antigen of the invention comprised in the immunogenic composition and the "test" sequence is the sequence present in the particular influenza virus strain from which the influenza virus antigen of the infection may be derived. For example, the test sequence, e.g. a HA1, may be compared to the reference sequence, e.g. a fragment of a HA1 comprised in the immunogenic composition. The full length of the reference sequence is aligned with the test sequence. If the entire length of the reference sequence is 90% identical to a portion or the full length of the test sequence then the reference sequence is considered to be derived from the strain containing the test sequence. The sequences may be amino acid sequences. If the test sequence is a fusion protein, part of the fusion protein may be derived from an influenza virus strain and that part of the protein (reference sequence) is compared to the test sequence.

Sequences can be compared using BLAST. Software for performing BLAST analyses is publicly available through the National Center for Biotechnology Information (http://www.ncbi.nlm.nih.gov/).

Influenza Strains

The immunogenic composition of the invention comprises influenza antigens derived from at least 5 influenza strains. An influenza strain is classified according to the host species of origin, the year of isolation, geographic origin and serial number. Also, for influenza type A, the influenza strain is also classified by the serological properties of the subtypes of HA and NA.

The at least 5 influenza strains may all be the same type of influenza, or may be more than one type of influenza. Each influenza strain may be independently a type A, type B, type C or type D. Preferably, one or more or all of the influenza strains are strains of influenza currently circulating and/or have been circulating in the past 10 years. Preferably, at least one of the influenza strains is a type A influenza. Preferably at least one of the influenza strains is a type B influenza. More preferably, at least one of the influenza strains is a type A influenza and at least one of the influenza strains is a type B influenza. One or more of the influenza strains may be an influenza type A strain with any of the HA subtypes such as HA1, HA2, HA3, HA4, HA5, HA6, HA7, HA8, HA9, HA10, HA11, HA12, HA13, HA14, HA15, HA16, HA17 or HA18 and/or any of the NA subtypes such as NA1, NA2, NA3, NA4, NA5, NA6, NA7, NA8 or NA9. The influenza type A strain may be H1N1, H5N1, H3N2, H7N7, H7N9, H1N2, H2N2, H7N3, H5N2, H1N7, H9N2, H7N2 or H10N7. Preferably the influenza type A strain is H1N1 or H3N2. Of the at least 5 influenza strains, there may be more than one influenza type A strain which is the same subtype. Of the at least 5 influenza strains, there may be more than one subtype of influenza type A. Preferably, at least one of the strains is H1N1 and at least one of the strains is H3N2. Examples of influenza strains which could be included in the immunogenic composition are 07/102 A/Solomon Islands/3/2006 (H1N1) (IVR-145), 02/336 A/New Caledonia, 08/100 A/Brisbane/59/2007 (IVR-148) (H1N1), 08/140 B/Florida/4/2006, 08/184 B/Malaysia/2506/2004, 09/174 A/California/7/09 (H1N1)(NYMCX-179A), 09/310 A/Wisconsin/15/2009 (H3N2)(NYMCX-183), 12/110 B/Wisconsin/1/2010 (Cell Derived), 12/112 A/Victoria/210/2009 (H3N2)(NYMCX-187), 12/114 A/Victoria/361/2011 (H3N2)(IVR-165), 13/134 B/Massachusetts/02/2012, 13/162 A/Texas/50/2012 (H3N2)(NYMCX-223A), 13/234 B/Brisbane/60/08, 14/252 B/Phuket/3073/2013, and 14/254 A/Switzerland/9715293/2013 (NIB88), all of which may be included in the immunogenic composition. (Bold underline=Influenza Resource Centre (IRC) of the NIBSC identification.) Examples of influenza strain subtypes which could be included in the immunogenic composition are H1N1, H3N2, H5N1, H5N6, H7N7, H7N9 and H9N2, all of which may be included in the immunogenic composition. The influenza virus strains may each be seasonal or pandemic strains, or may be a combination of seasonal and pandemic strains.

Preparing the Immunogenic Composition

The invention provides a method of preparing the immunogenic composition. The immunogenic composition is prepared by freezing, heat-treating and/or freeze-drying the influenza antigens when in the aqueous composition(s), which also comprises the one or more compound(s). The influenza antigen is typically admixed with the compound(s) to give one or more aqueous composition(s), and the aqueous composition(s) are then subjected to a treatment, such as freezing, heat-treating and/or freeze-drying, that increases the immunogenicity of the influenza antigen. Freezing, heat-treating and/or freeze-drying the influenza antigen in the presence of the compound(s) increases the immunogenicity of the antigen as compared to that observed if the influenza antigen is merely mixed with the compound(s) without freezing, heat-treating and/or freeze-drying.

The immunogenic composition may be prepared using a single aqueous composition which comprises the influenza virus antigens. The immunogenic composition may alternatively be prepared using two or more aqueous compositions, each of which comprises at least one influenza virus antigen and at least one of the one or more compound(s), and subsequently combining the resulting treated compositions. The "resulting treated compositions" are the compositions which result from freezing, heat-treating and/or freeze-drying. The or each aqueous composition may undergo one or more types of treatment. One or more aqueous composition(s) may undergo a different treatment or treatment combination than one or more other aqueous composition(s).

The influenza virus antigen(s) and compound(s) interact during the treatment, thereby to increase the immunogenicity of the influenza virus antigen(s), as compared to the immunogenicity of the influenza virus antigen(s) prior to the treatment. The immunogenicity of the antigen is therefore typically increased during the treatment step.

Typically, the treatment is freezing or heat-treating or freeze-drying, preferably heat-treating. Alternatively, a combination of treatments may be used, such as freezing followed by heat-treating, or freeze-drying followed by heat-treating. In the latter case, the freeze-dried composition would typically be reconstituted prior to heat-treating.

The resulting composition can be can be thawed, reconstituted or cooled after freezing, freeze-drying or heat-treating respectively, and administered as a immunogenic composition, pharmaceutical composition or vaccine composition.

As described herein, the aqueous composition may comprise all the influenza virus antigens prior to freezing, heat-treating and/or freeze-drying, or, alternatively, one or more of the influenza virus antigen(s) may undergo the freezing, heat-treating and/or freeze-drying in separate aqueous compositions and then combined to form the immunogenic composition. Thus one or more influenza antigens may be undergo treatment separately and are then combined.

The immunogenic composition can be prepared by individual adsorption of each influenza antigen to Alhydrogel by methods of those skilled in the art (e.g. exemplified in the Example herein) with subsequent generation of a bulk multivalent pooled blend to which the chemical components mannitol, DMG and TMG can be added.

Aqueous Composition(s)

There may be more than one aqueous composition. It there is one aqueous composition, the single aqueous composition comprises the compound(s) and the influenza virus antigens. The single aqueous composition may comprise all the influenza antigens prior to freezing, heat-treating and/or freeze-drying. If there are two or more aqueous compositions, then the two or more aqueous compositions each comprise at least one of the influenza virus antigens and at least one of the compound(s). Thus one or more of the influenza antigens may undergo the freezing, heat-treating and/or freeze-drying in separate aqueous compositions and are then combined to form the immunogenic composition. There may be the same number of aqueous compositions as there are influenza virus antigens. There may be fewer aqueous compositions as there are influenza virus antigens as there may be more than one influenza virus antigen in any individual aqueous composition. The description herein of the aqueous composition may apply independently to each aqueous composition.

The aqueous composition(s) is typically a suspension or solution. The aqueous composition(s) may be prepared by admixing the compound(s) with the influenza virus antigen(s) in an aqueous solvent. Any suitable aqueous solvent-system may be used. The aqueous solvent may be buffered water. The aqueous solvent is typically HEPES-buffered water, Tris-buffered water, phosphate-buffered water or pure water.

Optionally, one or more sugars is admixed with the aqueous solvent prior to admixture with the compound(s) and influenza virus antigen(s). Alternatively the one or more sugars can be admixed with aqueous solvent after the compound(s) and influenza virus antigen(s).

Optionally, an adjuvant is admixed with the aqueous solvent prior to admixture with the compound(s) and influenza virus antigen(s). Alternatively the adjuvant can be admixed with aqueous solvent after the compound(s) and influenza virus antigen(s).

Typically, if an adjuvant is present, one or more sugars will also be present, since the one or more sugars will generally stabilise the adjuvant, particularly during the treatment step.

Other components may also be present in the aqueous composition(s). For example, a compound of formula (II) may also be present:

(II)

wherein X represents —S(O)$_2$— and R$_a$ and R$_b$ independently represent C$_{1-6}$ alkyl. A preferred compound of formula (II) is methylsulfonylmethane (MSM) in which R$_a$ and R$_b$ both represent methyl. The combination of the one or more compound(s) and compound of formula (II) may interact together, thereby to further increase the immunogenicity of the influenza antigen during the treatment step.

The concentration of the one or more compound(s) in the aqueous composition(s) is typically in the range of 0.001M or more, preferably in the range of 0.01M or more and more preferably 0.1M or more, for example from 0.1M to 5.0M, or about 0.5M. Preferably, the immunogenic composition comprises 0.3M to 0.5M of one compound of the invention and 0.3M to 0.5M of another compound of the invention. More preferably, the immunogenic composition comprises about 0.4M of one compound of the invention and about 0.4M of another compound of the invention.

If one or more sugar(s) is used, the concentration of sugar or total concentration of sugar in the aqueous composition(s) is typically 1M or less, preferably 0.7M or less, for example 0.5M or less or 0.3M or less. The sugar concentration or the total concentration may be down to 0.1 mM or to 0.5 mM. The sugar concentration or the total concentration may be 0.5M to 0.7M, preferably about 0.6M.

The particular concentration of each component that is employed will depend on several factors including the nature of the influenza virus antigen(s); the compound(s) being used; whether one or more sugar is being used and if so the identity of the sugar(s); whether or not an adjuvant is present; and the particular freezing, freeze-drying or heat treatment procedure that is adopted.

The Compound(s)

The immunogenic composition of the invention comprises one or more compound(s) of formula (I) or physiologically acceptable salts or esters thereof. The description herein of the compound may apply independently to each compound. There may be 2, 3, 4 or more compounds present. There may be 1 to 3 compounds present. There are preferably 2 compounds present.

The physiologically acceptable salt is typically a salt with a physiologically acceptable acid and thus includes those formed with an inorganic acid such as hydrochloric or sulphuric acid or an organic acid such as citric, tartaric, malic, maleic, mandelic, fumaric or methanesulphonic acid. The hydrochloride salt is preferred.

The ester is typically a C$_{1-6}$ alkyl ester, preferably a C$_{1-4}$ alkyl ester. The ester may therefore be the methyl, ethyl, propyl, isopropyl, butyl, isobutyl or tert-butyl ester. The ethyl ester is preferred.

As used herein, a C$_{1-6}$ alkyl group is preferably a C$_{1-4}$ alkyl group. Preferred alkyl groups are selected from methyl, ethyl, propyl, isopropyl, butyl, isobutyl and tert-butyl. Methyl and ethyl are particularly preferred.

For the avoidance of doubt, the definitions of compounds of formula (I) also include compounds in which the carboxylate anion is protonated to give —COOH and the ammonium cation is associated with a pharmaceutically acceptable anion. Further, for the avoidance of doubt, the compounds defined above may be used in any enantiomeric form.

Typically, $R_1$ represents hydrogen or $C_{1-4}$ alkyl, preferably hydrogen or $C_{1-3}$ alkyl, more preferably hydrogen, ethyl or methyl, most preferably hydrogen or methyl.

Typically, $R_2$ represents $C_{1-4}$ alkyl, preferably $C_{1-3}$ alkyl, more preferably ethyl or methyl, most preferably methyl.

Typically, $R_3$ represents $C_{1-4}$ alkyl, preferably $C_{1-3}$ alkyl, more preferably ethyl or methyl, most preferably methyl.

$R_2$ and $R_3$ may be the same or different, but are preferably the same. When $R_1$ represents $C_{1-6}$ alkyl, then $R_1$, $R_2$ and $R_3$ may be the same or different, but are preferably the same.

In a preferred embodiment, $R_1$ represents hydrogen and $R_2$ and $R_3$ are as defined above. Thus, it is particularly preferred that $R_1$ represents hydrogen and $R_2$ and $R_3$ represent methyl, such that the compound of formula (I) is dimethylglycine.

In an alternative preferred embodiment, $R_1$ represents $C_{1-6}$ alkyl and $R_2$ and $R_3$ are as defined above. Thus, it is particularly preferred that $R_1$ to $R_3$ all represent methyl, such that the compound of formula (I) is trimethylglycine.

In a preferred embodiment, the immunogenic composition comprises both dimethylglycine (DMG) and trimethylglycine (TMG). More preferably, the immunogenic composition comprises about 0.4M of DMG and about 0.4M of TMG.

Sugars

One or more sugars is optionally present in the or each aqueous composition. If there is more than one aqueous composition, the sugars present in each aqueous composition may be different or the same. Two or more sugars may be present, for example two, three or four sugars. It is preferred that one or two sugars is present, most preferably two sugars. The combination of compound(s) and sugar(s) may interact together, thereby to increase further the immunogenicity of the influenza antigen during the treatment step. The sugar(s) also assist in stabilising the adjuvant when present, particularly aluminium salt adjuvants, during the treatment step.

The sugar is typically a monosaccharide, a disaccharide, a trisaccharide, a tetrasaccharide, a sugar alcohol or another oligosaccharide.

Typically, the monosaccharide is glucose, fructose, arabinose, glyceraldehydes, galactose or mannose. Typically, the dissaccharide is sucrose, trehalose, lactose, cellobiose, turanose, maltulose, melibiose, isomaltose, or maltose. Typically, the trisaccharide is raffinose, melezitose or umbelliferose. Typically, the tetrasaccharide is stachyose. Typically, the sugar alcohol is mannitol. Other examples of oligosaccharides include the pentasaccharide verbascose.

Typically, the sugar is a non-reducing sugars, for example sucrose or raffinose.

When one sugar is present in the aqueous solution, the sugar is preferably mannitol or sucrose, preferably mannitol.

When two sugars are present in the aqueous suspension, the sugars are preferably sucrose and raffinose.

Adjuvant

An adjuvant is optionally present in the or each aqueous composition(s) and/or in the immunogenic, pharmaceutical or vaccine composition. Any suitable adjuvant may be used, but aluminium salt adjuvants are preferred. When an aluminium salt adjuvant is used, it is preferred that one or more sugars is also present in the or each aqueous composition(s), to stabilise the adjuvant during the treatment step.

Typically, the aluminium salt adjuvant is aluminium hydroxide ($Al(OH)_3$), aluminium phosphate ($AlPO_4$), aluminium hydrochloride, aluminium sulphate, ammonium alum, potassium alum or aluminium silicate. Preferably, the aluminium salt adjuvant used is aluminium hydroxide or aluminium phosphate. Most preferably, the aluminium salt adjuvant is aluminium hydroxide ($Al(OH)_3$).

Typically, the aluminium salt adjuvant takes the form of a hydrated gel made from an aluminium salt, the hydrated gel being a particulate suspension in aqueous media. The preparation of aluminium-salt adjuvants are well known to those skilled in the art. For example, aluminium hydroxide and aluminium phosphate adjuvants are generally prepared by exposing aqueous solutions of aluminium ions (typically as sulfates or chlorides) to alkaline conditions in a well-defined and controlled chemical environment, as known to those skilled in the art. Such methods can be used for example, to prepare an aluminium hydroxide or aluminium phosphate hydrated gel.

Freezing

Freezing of the or each aqueous composition can be conducted by any suitable method. Freezing may thus be carried out by immersing in liquid nitrogen or liquid nitrogen vapour, placing in a freezer or using a dry ice and alcohol freezing bath.

Typically, the or each aqueous composition is frozen to −4° C. or below, preferably −10° C. or below, more preferably to −20° C. or below, more preferably to −30° C. The or each aqueous composition is typically not frozen below −100° C. The or each aqueous composition may, for example, be frozen to about −80° C.

The or each aqueous composition is typically kept frozen at the desired temperature for 30 minutes or more, preferably 1 hour or more, for example from 2 to 24 hours.

The or each frozen aqueous composition is typically allowed to thaw by leaving at room temperature before use as an immunogenic composition, pharmaceutical composition or vaccine.

The freezing and thawing conditions can be suitably optimised via routine experimentation.

Freeze-Drying

Freeze-drying can be carried out according to standard procedures. There are three main stages: freezing, primary drying and secondary drying. Freezing is typically performed using a freeze-drying machine. In this step, it is important to cool the biological material below its eutectic point, the lowest temperature at which the solid and liquid phase of the material can coexist. This ensures that sublimation rather than melting will occur in the following steps. Alternatively, amorphous materials do not have a eutectic point, but do have a critical point, below which the product must be maintained to prevent melt-back or collapse during primary and secondary drying.

During primary drying the pressure is controlled by the application of appropriate levels of vacuum whilst enough heat is supplied to enable the water to sublimate. At least 50%, typically 60 to 70%, of the water in the material is sublimated at this stage. Primary drying may be slow as too much heat could degrade or alter the structure of the biological material. A cold condenser chamber and/or condenser plates provide surfaces on which the water vapour is trapped by resolidification.

In the secondary drying process, water of hydration is removed by the further application of heat. Typically, the pressure is also lowered to encourage further drying. After completion of the freeze-drying process, the vacuum can either be broken with an inert gas such as nitrogen prior to sealing or the material can be sealed under vacuum.

The freeze-dried composition is reconstituted as an aqueous composition, using for example water or an aqueous buffer, before use as a vaccine.

The freeze-drying conditions can be suitably optimised via routine experimentation.

Heat-Treating

Heat-treating of the or each aqueous composition can be conducted by any suitable method.

Typically, the or each aqueous composition is heated to greater than 30° C., preferably greater than 40° C. More preferably, the or each aqueous composition is heated to a temperature of 30° C. to 80° C., for example 35° C. to 60° C. or 40° C. to 50° C. A preferred temperature is about 45° C.

Once the or each aqueous composition has been heated to the desired temperature, the or each aqueous composition is preferably maintained at that temperature for 30 minutes or more, preferably 1 hour or more, for example from 2 hours to 2 weeks or from 4 hours to 24 hours.

A typical heat treatment involves heating to about 45° C. and maintaining at that temperature for about 7 days.

The or each heat treated aqueous composition is typically allowed to return to room temperature before use as a vaccine.

The heat treatment conditions can be suitably optimised via routine experimentation.

Increase in Immunogenicity

The immunogenicity of the influenza virus antigen is the ability of that antigen to provoke an immune response in the body of an animal, such as human. A change in immunogenicity can be measured by comparing the immunogenicity of an untreated (control) influenza antigen with the immunogenicity of an influenza virus antigen which has been treated in accordance with the invention, using a standard assay for predicting the level of immune response. The immunogenicity of an influenza virus antigen can be measured using any suitable technique known to those skilled in the art, such as those described herein. A preferred standard technique is the haemmagglutination inhibition assay. An exemplary protocol for this assay is set out in the Example below.

Use of heat-treating, freezing or freeze-drying the aqueous composition(s) comprising the compound(s) and influenza virus antigens of the invention increases the immunogenicity of the influenza virus antigens. The increased immunogenicity of the influenza virus antigens of the inventions means that the same immune response can be obtained with a smaller amount of influenza virus antigen. Thus, if a patient is administered a dose D of untreated influenza virus antigen and dose D achieves a level of immunogenicity, then typically a dose of treated influenza virus antigen of 0.5 D or less, preferably 0.1 D or less, more preferably 0.01 D or less, will achieve the same level of immunogenicity. The immunogenicity is typically measured at least 10 days after administration to the patient, for example after 10 days, 15 days or 20 days.

The increased immunogenicity of the treated influenza virus antigens of the invention means that the onset of immunity occurs more quickly than with untreated influenza virus antigens. Thus, if a patient takes a time T to acquire immunity following administration of a given dose of untreated antigens, then it will typically take 0.75 T or less time, preferably 0.5 T or less time, most preferably 0.2 T or less time, for a patient administered the same dose of treated antigens to acquire immunity.

The following Example illustrates the invention.

Example

A multivalent influenza composition was prepared composed of the following 15 influenza antigen strains: 07/102 A/Solomon Islands/3/2006 (H1N1) (IVR-145), 02/336 A/New Caledonia, 08/100 A/Brisbane/59/2007 (IVR-148) (H1N1), 08/140 B/Florida/4/2006, 08/184 B/Malaysia/2506/2004, 09/174 A/California/7/09 (H1N1)v (NYMCX-179A), 09/310 A/Wisconsin/15/2009 (H3N2)(NYMCX-183), 12/110 B/Wisconsin/1/2010 (Cell Derived), 12/112 A/Victoria/210/2009 (H3N2)(NYMCX-187), 12/114 A/Victoria/361/2011 (H3N2)(IVR-165), 13/134 B/Massachusetts/02/2012, 13/162 A/Texas/50/2012 (H3N2)(NYMCX-223A), 13/234 B/Brisbane/60/08, 14/252 B/Phuket/3073/2013, 14/254 A/Switzerland/9715293/2013 (NIB88). (Bold underline=Influenza Resource Centre (IRC) of the NIBSC identification).

Materials and Methods

HEPES buffer was prepared as follows: 20 ml of sterile water was measured out in a cylinder. 0.0437 g NaCl was weighed out on a calibration checked balance and dissolved in the sterile water using a magnetic stirrer and bar. 1.2 ml of 1M HEPES was added and stirred. When fully dissolved, a pH meter and sodium hydroxide were used to alter the pH to 7.9. The final volume was made up to 30 ml with sterile water. The final HEPES buffer mix was then filtered through a 0.2 μm filter unit in a biological safety cabinet.

The components (referred to in the Example as the "excipient components") DMG (1.237 g), TMG (1.406 g) and Mannitol (3.276 g) were weighed out and then placed into a 50 ml sterile flask. Approximately 6 ml of the HEPES buffer was then added to the flask and the contents were mixed by swirling. The flask and contents were then heated in a +60° C. water bath until dissolved. When dissolved, the volume of the mix was measured and the final volume made up to 10 ml with more HEPES buffer. The excipient formulation was filtered through a 0.2 μm filter unit in a biological safety cabinet.

Vials of freeze-dried influenza virus antigen strains 07/102 A/Solomon Islands/3/2006 (H1N1) (IVR-145), 02/336 A/New Caledonia, 08/100 A/Brisbane/59/2007 (IVR-148)(H1N1), 08/140 B/Florida/4/2006, 08/184 B/Malaysia/2506/2004, 09/174 A/California/7/09 (H1N1) (NYMCX-179A), 09/310 A/Wisconsin/15/2009 (H3N2) (NYMCX-183), 12/110 B/Wisconsin/1/2010 (Cell Derived), 12/112 A/Victoria/210/2009 (H3N2)(NYMCX-187), 12/114 A/Victoria/361/2011 (H3N2)(IVR-165), 13/134 B/Massachusetts/02/2012, 13/162 A/Texas/50/2012 (H3N2) (NYMCX-223A), 13/234 B/Brisbane/60/08, 14/252 B/Phuket/3073/2013, 14/254 A/Switzerland/9715293/2013 (NI1388) were allowed to reach room temperature from −20° C. and working stocks of the antigen in sterile water were prepared. Each individual influenza virus antigen component was added volumetrically 1 part influenza virus antigen to 1.292 parts Alhydrogel (2% initial concentration) for absorption, which was performed on rocker plate (50 rpm) for 1 hour at RT (50 rpm), and stationary overnight at 4° C. Following absorption, the individual influenza virus antigen components were pooled to make a multivalent composition into a screw capped vial to which the excipient components and additional HEPES buffer added, volumetric parts being 1 part influenza virus antigen pool, 1.162 parts excipient components and 1.382 parts HEPES buffer yielding a total 3 ml volume. The total volume was then stored at 45° C. for 5 days as a nominal heat treatment process. The final vaccine composition preparation contained 0.32% Alhydrogel, 0.6M Mannitol, 0.4M DMG, 0.4M TMG with an individual influenza virus antigen component concentration of 1.252 µg/ml and a total antigen concentration of 18.78 µg/ml.

After the heat treatment, the vaccine composition preparation then returned to refrigerated storage prior to administration subcutaneously (0.1 ml dose volume) to BALB-c mice at day 0 and day 28. The protective effects of the compositions against influenza strains were determined at various time points by measuring the HAI titre in sera obtained from the BALB-c mice at day −7 (pre vaccine administration), day 11, day 25, day 35 and day 45.

HAI assays were performed as per WO2015/155527 A1, page 19 subject to the following amendment of line 11 (Step 1). In Step 1 in WO2015/155527 at page 19, the sera was inactivated at 56° C. for 30 minutes. However, in the present case, in Step 1, the sera was inactivated by Receptor Destroying Enzyme treatment, followed by heating at 56° C. for 30 minutes.

Results

Figure 1:
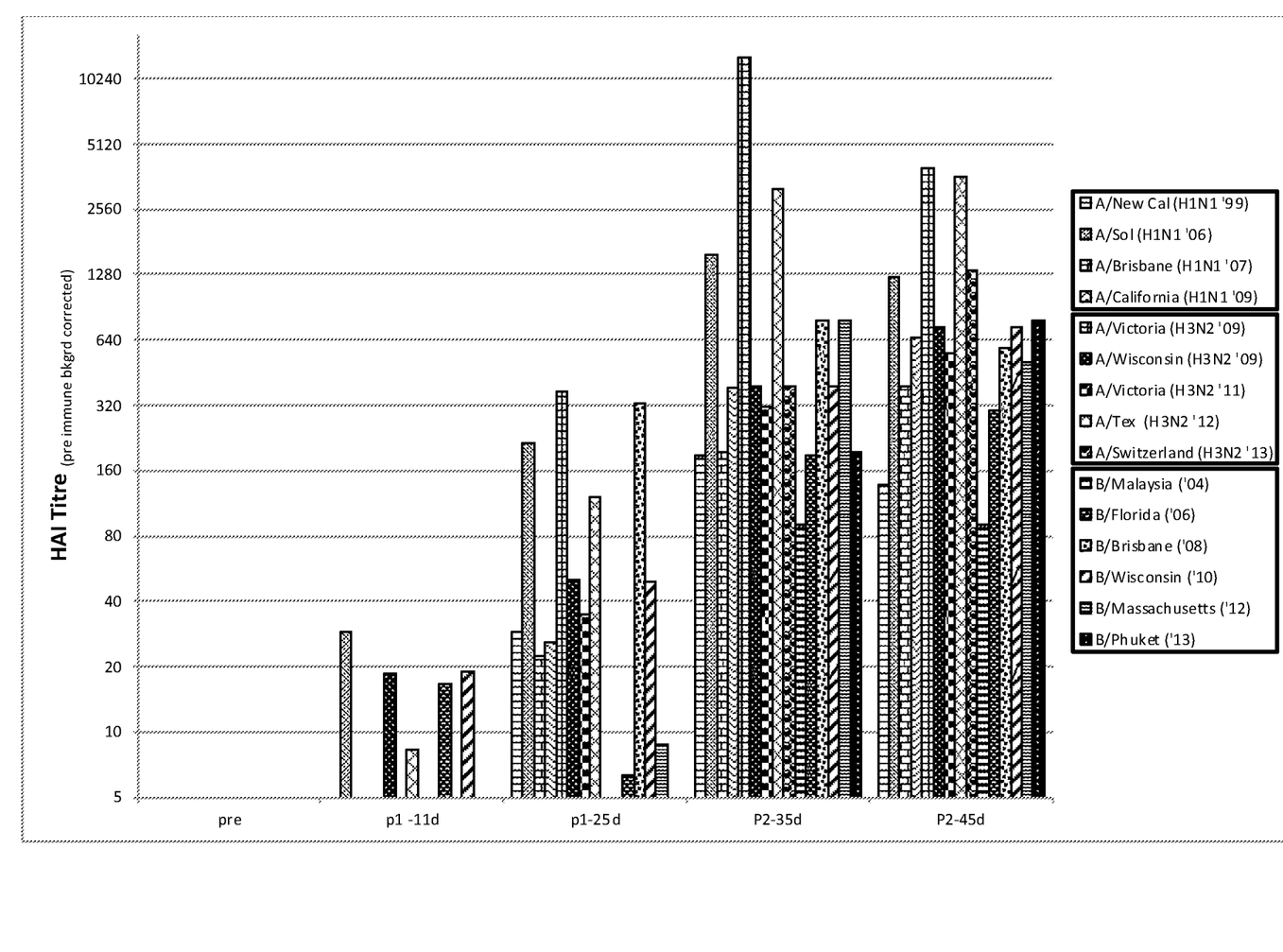
FIG. 1 shows the results of a haemagglutinin inhibition assay (HAI) for a multivalent composition comprising antigens derived from 15 strains of influenza administered to BALB-c mice at day 0 and day 28. The HAI titre was measured in sera obtained from the mice at day −7 (i.e. 7 days prior to the first administration) and at day 11, day 25, day 35 and day 45. The measurement from day −7 was deducted from each day 11, day 25, day 35 and day 45 to correct for background pre-immunisation non-specific HAI activity intrinsically present in the sera. The bars from left to right for each time point correspond to the influenza strains listed in the legend from top to bottom.

The HAI results exemplified (in mice) a 15 valent influenza subcutaneous vaccine which generates HAI titres of greater than 40 against all A/B strain tested (see FIG. 1). Immune reactions of 14 of the 15 strains have been measured. The 15$^{th}$ strain (A/Victoria/361/2011) is expected to show the same results. HAI titres equal to or greater than 40 post background correction are considered to indicate a protective immunity response level (Skountzou, Ioanna et al. "Influenza Virus-Specific Neutralizing IgM Antibodies Persist for a Lifetime." Ed. S. A. Plotkin. Clinical and Vaccine Immunology: CVI 21.11 (2014): 1481-1489. PMC.). The vaccine included influenza antigens derived from cell culture and egg derived sources. It is anticipated that the vaccine could provide cross protection against other influenza strains of the same subtype. The vaccine has the potential to provide an influenza vaccine against all strains types A, B, C and D inclusive of all subtypes together with antigenic drift variants. This may eliminate the requirement for annually redesigning the seasonal influenza vaccine.

The invention claimed is:

1. An immunogenic composition comprising influenza virus antigens derived from at least 5 influenza virus strains and one or more compounds of formula (I) or a physiologically acceptable salt or ester thereof:

(I)

wherein:
R$_1$ represents hydrogen or C$_{1-6}$ alkyl;
R$_2$ represents C$_{1-6}$ alkyl; and
R$_3$ represents C$_{1-6}$ alkyl.

2. The immunogenic composition according to claim 1, comprising influenza virus antigens derived:
from 20 or less influenza virus strains, or
from at least 6 influenza virus strains, or
from 8 to 18 influenza virus strains, or
from 14 to 18 influenza virus strains, or
from 15 influenza virus strains, or
at least 2 influenza virus types, or
from at least 2 subtypes of influenza virus type A.

3. The immunogenic composition according to claim 1, comprising at least one influenza virus antigen derived from a type A influenza virus strain and at least one influenza virus antigen derived a type B influenza virus strain.

4. The immunogenic composition according to claim 1, comprising influenza virus antigens derived from at least 2 subtypes of influenza virus type A.

5. The immunogenic composition according to claim 1, comprising at least one influenza virus antigen derived from a H1N1 subtype of a type A influenza virus strain and at least one influenza virus antigen derived a H3N2 subtype of a type A influenza virus strain.

6. The immunogenic composition according to claim 1, comprising influenza virus antigens derived from one or more of the following influenza virus strains:
07/102 A/Solomon Islands/3/2006 (H1N1) (IVR-145),
02/336 A/New Caledonia,
08/100 A/Brisbane/59/2007 (IVR-148)(H1N1),
08/140 B/Florida/4/2006,
08/184 B/Malaysia/2506/2004,
09/174 A/California/7/09 (H1N1)(NYMCX-179A),
09/310 A/Wisconsin/15/2009 (H3N2)(NYMCX-183),
12/110 B/Wisconsin/1/2010 (Cell Derived),
12/112 A/Victoria/210/2009 (H3N2)(NYMCX-187),
12/114 A/Victoria/361/2011 (H3N2)(IVR-165),
13/134 B/Massachusetts/02/2012,
13/162 A/Texas/50/2012 (H3N2)(NYMCX-223A),
13/234 B/Brisbane/60/08,
14/252 B/Phuket/3073/2013, and
14/254 A/Switzerland/9715293/2013 (NIB88).

7. The immunogenic composition according to claim 1, which comprises one or two compounds of formula (I) or physiologically acceptable salts or esters thereof.

8. The immunogenic composition according to claim 1, which comprises dimethylglycine or a pharmaceutically acceptable salt or ester thereof.

9. The immunogenic composition according to claim 8, which comprises dimethylglycine and trimethylglycine, or pharmaceutically acceptable salts or esters of one or both thereof.

10. The immunogenic composition according to claim 1, in which the influenza virus antigens have previously undergone (a) freezing, (b) heat-treating and/or (c) freeze-drying when in an aqueous composition additionally comprising the or each compound.

11. The immunogenic composition according to claim 1, in which the immunogenic composition further comprises one or more sugars.

12. The immunogenic composition according to claim 1, in which the immunogenic composition comprises one sugar which is mannitol.

13. The immunogenic composition according to claim 1, in which the immunogenic composition further comprises an adjuvant.

14. The immunogenic composition according to claim 13, in which the adjuvant is an aluminium salt adjuvant.

15. An immunogenic composition according to claim 1, obtainable by a method comprising (a) freezing, (b) heat-treating, and/or (c) freeze-drying (i) a single aqueous composition which comprises the influenza virus antigens and the compound(s), or (ii) two or more aqueous compositions, each of which comprises at least one influenza virus antigen and at least one compound(s), and subsequently combining the resulting treated compositions.

16. A method of inducing an immune response against an influenza virus in a subject, which method comprises administering to the subject an effective amount of an immunogenic composition, the composition comprising influenza virus antigens derived from at least 5 influenza virus strains and one or more compounds of formula (I) or a physiologically acceptable salt or ester thereof:

(I)

wherein:
R$^1$ represents hydrogen or C$_{1-6}$ alkyl;
R$_2$ represents C$_{1-6}$ alkyl; and
R$_3$ represents C$_{1-6}$ alkyl.

17. A method of preventing an influenza virus in a subject, which method comprises administering to the subject an effective amount of an immunogenic composition, the composition comprising influenza virus antigens derived from at least 5 influenza virus strains and one or more compounds of formula (I) or a physiologically acceptable salt or ester thereof:

(I)

wherein:
R$_1$ represents hydrogen or C$_{1-6}$ alkyl;
R$_2$ represents C$_{1-6}$ alkyl; and
R$_3$ represents C$_{1-6}$ alkyl.

* * * * *